US009074241B2

(12) United States Patent
Estibeiro et al.

(10) Patent No.: US 9,074,241 B2
(45) Date of Patent: Jul. 7, 2015

(54) METHODS EMPLOYING NON-CODING RNA EXPRESSION ASSAYS

(75) Inventors: Jacinto Peter Estibeiro, Gorebridge (GB); John Francis Gordon, Tayport (GB); Christopher Robert Hillier, Glasgow (GB); Vincent O'Brien, Ayr (GB)

(73) Assignee: Sistemic Scotland Limited, Edinburgh (GB)

( * ) Notice: Subject to any disclaimer, the term of this patent is extended or adjusted under 35 U.S.C. 154(b) by 721 days.

(21) Appl. No.: 13/145,208

(22) PCT Filed: Jan. 19, 2010

(86) PCT No.: PCT/GB2010/000076
§ 371 (c)(1),
(2), (4) Date: Sep. 7, 2011

(87) PCT Pub. No.: WO2010/082039
PCT Pub. Date: Jul. 22, 2010

(65) Prior Publication Data
US 2011/0312524 A1     Dec. 22, 2011

(30) Foreign Application Priority Data

Jan. 19, 2009  (GB) .................................. 0900809.5
Oct. 9, 2009   (GB) .................................. 0917708.0

(51) Int. Cl.
*C12Q 1/68* (2006.01)

(52) U.S. Cl.
CPC .................................... *C12Q 1/6809* (2013.01)

(58) Field of Classification Search
None
See application file for complete search history.

(56) References Cited

U.S. PATENT DOCUMENTS

| 8,367,318 B2* | 2/2013 | Smith et al. .................... 435/325 |
| 8,637,254 B2* | 1/2014 | Taylor et al. .................. 435/6.14 |
| 2005/0266552 A1 | 12/2005 | Doench |
| 2009/0099034 A1 | 4/2009 | Ahlquist et al. |
| 2010/0178653 A1 | 7/2010 | Aharonov et al. |
| 2010/0310583 A1 | 12/2010 | Lieberman et al. |
| 2010/0323357 A1* | 12/2010 | Nana-Sinkam et al. .......... 435/6 |

FOREIGN PATENT DOCUMENTS

| WO | 2008/095096 | 8/2008 |
| WO | 2008/117278 | 10/2008 |
| WO | 2008/154098 | 12/2008 |

OTHER PUBLICATIONS

Sorrentino et al. "Role of microRNAs in drug-resistant ovarian cancer cells" *Gynecologic Oncology*, vol. 111, No. 3, pp. 478-486, abstract 152 (Dec. 2008).
Examination report for related European application, Serial No. 12169171.1, six pages, mailed Jul. 26, 2013.
Illmer et al. "MiRNA expression signatures in acute myeloid leukemia are predictors for patient outcome" *Blood*, vol. 108, No. 11, p. 49A, abstract 152 (Nov. 2006).
Lakshmipathy et al. "Micro RNA profiling: An easy and rapid method to screen and characterize stem cell populations" from *Methods in Molecular Biology, Stem Cell Assays*, Humana Press, Totowa, NJ, vol. 407, pp. 97-114 (Aug. 2007).
Lakshmipathy et al. "MicroRNA expression pattern of undifferentiated and differentiated human embryonic stem cells" *Stem Cells and Development*, vol. 16, No. 6, pp. 1003-1016 (Dec. 2007).
Silber et al. "miR-124 and miR-137 inhibit proliferation of glioblastoma multiforme cells and induce differentiation of brain tumor stem cells" *BMC Medicine*, vol. 6, No. 14, pp. 1-17 (Jun. 2008).
Supplementary search report for related European application, Serial No. 12169171.1, five pages, mailed Jun. 14, 2012.
Int'l Search Report for PCT/GB2010/000076, five pages, mailed May 12, 2010.
Barad et al. "MicroRNA expression detected by oligonucleotide microarrays: System establishment and expression profiling in human tissues" *Genome Research*, vol. 14, No. 12, pp. 2486-2494, Dec. 2004.
Krutzfeldt et al. "Silencing of microRNAs in vivo with antagomirs" *Nature*, vol. 429, pp. 685-689, Dec. 2005.
Liu et al. "Microarray-based analysis of stressed-regulated microRNAs in *Arabidopsis thaliana*" *RNA*, vol. 14, No. 5, pp. 836-843, May 2008.
Moschos et al. "Expression profiling in vivo demonstrates rapid changes in lung microRNA levels to following lipopolysaccharaide-induced inflammation but not in the anti-inflammatory action of glucocorticoids" *BMC Genomics*, 8:240, 12 pages, Jul. 2007.
Perera "A microarray-based method to profile global microRNA expression in human and mouse" *Methods in Molecular Biology*, vol. 382, pp. 137-148, Jan. 2007.

(Continued)

*Primary Examiner* — Jim Ketter
(74) *Attorney, Agent, or Firm* — The Marbury Law Group PLLC (57) ABSTRACT

There is disclosed a method comprising the steps of: carrying out a plurality of expression assays, each expression assay comprising the steps of: carrying out an intervention on a biological system, measuring an expression profile of non-coding RNAs in the biological system resulting from the intervention, and storing an expression data set derived from the measured expression profile, the said expression assays concerning either or both a plurality of different interventions and a plurality of different biological systems; and analysing the resulting expression data sets to determine correlations between the effect on the expression profile of non-coding RNAs of the respective intervention in groups of two or more expression assays concerning either or both different interventions or different biological systems.

5 Claims, 4 Drawing Sheets

(56) References Cited

OTHER PUBLICATIONS

Moschos et al. "Expression profiling in vivo demonstrates rapid changes in lung microRNA levels to following lipopolysaccharaide-induced inflammation but not in the anti-inflammatory action of glucocorticoids" *BMC Genomics*, 8:240, 12 pages, Jul. 2007.
Int'l Search Report for PCT/GB2010/000076, six pages, mailed May 12, 2010.
Written Opinion for PCT/GB2010/000076, seven pages, mailed May 12, 2010.
Int'l Preliminary Report on Patentability for PCT/GB2010/000076, eight pages, mailed Jul. 19, 2011.
Blower et al. "MicroRNAs modulate the chemosensitivity of tumor cells" *Mol. Cancer Ther*. vol. 7, No. 1, pp. 1-9, Jan. 2008.
Gaedicke et al. "Vitamin E dependent microRNA regulation in rat liver" *FEBS Lett*. vol. 582, Nos. 23-24, pp. 3542-3546, Oct. 2008.
Pogribny et al. "Induction of microRNAome deregulation in rat liver by long-term tamoxifen exposure" *Mutation Res*. vol. 619, Nos. 1-2, pp. 30-37, Jun. 2007.
Rossi et al. "Modification of miR gene expression pattern in human colon cancer cells following exposure to 5-fluorouracil in vitro" *Pharmacol.Res*. vol. 56, No. 3, pp. 248-253, Sep. 2007.
Scott et al. "Rapid alteration of microRNA levels by histone deacetylase inhibition" *Cancer Res*. vol. 66, No. 3, pp. 1277-1281, Feb. 2006.
Sun et al. "Curcumin (diferuloylmethane) alters the expression profiles of microRNAs in human pancreatic cancer cells" *Mol. Cancer Ther*. vol. 7, No. 3, pp. 464-731, Mar. 2008.

* cited by examiner

| Micro RNA | p-Value | q-Value |
|---|---|---|
| hsa-miR-1 | 4.86E-06 | 0.004281 |
| hsa-miR-2 | 2.04E-05 | 0.004741 |
| hsa-miR-3 | 1.96E-05 | 0.004741 |
| hsa-miR-4 | 2.15E-05 | 0.004741 |
| hsa-miR-5 | 5E-05 | 0.007338 |
| hsa-miR-6 | 4.43E-05 | 0.007338 |
| hsa-miR-7 | 0.000127 | 0.015941 |
| hsa-miR-8 | 0.000333 | 0.036713 |
| hsa-miR-9 | 0.000403 | 0.039477 |
| hsa-miR-10 | 0.000454 | 0.039981 |
| hsa-miR-11 | 0.001128 | 0.090341 |

METHODS EMPLOYING NON-CODING RNA EXPRESSION ASSAYS

This application is the U.S. national phase under 35 USC 371 of Int'l Application No. PCT/GB2010/000076, filed on 19 Jan. 2010, which designated the U.S., and claims priority benefit to Application Nos. GB 0900809.5, filed on Jan. 19, 2009, and GB 0917708.0, filed on Oct. 9, 2009. The entire contents of each of the foregoing are incorporated by reference herein.

FIELD OF THE INVENTION

The invention concerns methods employing non-coding RNA expression assays. Embodiments of the invention addresses problems including, but not limited to, determining similarities in the mechanism by which two or more interventions affect biological systems, identifying candidate therapeutic applications of test agents and identifying new applications of therapeutic agents which have previously been the subject of clinical trials in respect of one or more indications.

BACKGROUND TO THE INVENTION

Issues concerning the invention will now be discussed with reference to applications of microRNA (miRNA) expression assays, however, the invention may employ expression assays concerning other non-coding RNA molecules.

miRNAs are single-stranded RNA molecules having a length of around 21 to 23 nucleotides. miRNAs were first described by Victor Ambros in 1993 and since then over 2,000 papers on have been published on the subject of miRNAs. There are predicted to be about 1,000 miRNAs in humans of which around 600 have been described and experimentally validated to date, although some estimates place the figure at tens of thousands. However, a recent report, which sought to produce an expression atlas of miRNA in various human and rodent tissues and cell lines, reported that around 300 miRNAs accounted for 97% of all detected miRNAs.

miRNA is not translated into protein but instead regulates the expression of one or more other genes. Known biology currently shows that microRNAs target particular individual messenger RNAs (mRNAs) or groups of mRNAs, thereby preventing their translation or, less frequently, accelerating mRNA degradation. The mature single stranded miRNA molecule complexes with the RNA-Induced Silencing Complex (RISC) protein and binds to a partially complementary sequence within the 3' untranslated region (3'-UTR) of the protein coding mRNA from its target gene. Further proteins are recruited to form a silencing complex and the expression of the target gene product is repressed by a mechanism that blocks the translation of the mRNA.

Although much remains to be discovered about the biology of miRNAs and the composition and mechanism of the silencing complex it is apparent that miRNAs are involved in the regulation of many genes. MiRNAs are thought to regulate as many as 30% of all genes (Xie et al, 2005) at the translational level. An miRNA can regulate multiple genes and each gene can be regulated by multiple miRNAs. Tissue-specific expression of miRNAs is thought to guide commitment of cells to differentiate and/or actively maintain tissue identity. This wide-ranging influence and interplay between different miRNAs suggests that deregulated expression of a single miRNA or small sub-set of miRNAs may result in complex disease traits (Lim et al, 2005, Nature). More than 50% of known human miRNAs reside in genomic regions prone to alteration in cancer cells (Calin et al, 2004 PNAS, 101, 299-3004). Not surprisingly, the expression pattern of miRNAs change in cancer and other disease states. This information has begun to be used to classify and stage cancers, reveal biomarkers for prognosis and response and provide a critical determinant to guide therapeutic intervention, explain chemosensitivity and inform the mechanisms of chemoresistance by allowing the definition of specific miRNA expression patterns in cancer stem cells.

Applications of miRNAs to research and the development of possible new therapeutics have typically resulted from detailed and time consuming analysis of the mechanisms by which miRNA expression and processing is regulated and the mechanisms by which specific miRNAs regulate mRNA translation. Specific drug targets have been identified and research in connection with these drug targets in ongoing. However, although thorough, this research paradigm is time consuming and expensive.

Thus, the invention aims to provide alternative methods for discovering practical applications of interventions, such as the administration of a therapeutic agent, which do not require a detailed understanding of the mechanism of action of the intervention or the identification of a specific drug target. Some embodiments of the invention address the problem of determining new indications for known therapeutic entities or predicting pharmacological properties of test agents, such as aspects of their toxicological profile.

SUMMARY OF THE INVENTION

According to the present invention there is provided a method comprising the steps of:
(1) carrying out a plurality of expression assays, each expression assay comprising the steps of: carrying out an intervention on a biological system, measuring an expression profile of non-coding RNAs in the biological system resulting from the intervention, and storing an expression data set derived from the measured expression profile, the said expression assays concerning either or both a plurality of different interventions and a plurality of different biological systems; and
(2) analysing the resulting expression data sets to determine correlations between the effect on the expression profile of non-coding RNAs of the respective intervention in groups of two or more expression assays concerning either or both different interventions or different biological systems.

By analysing expression data sets to determine similarities between the effect of an intervention on the expression profile of non-coding RNAs in groups of two or more expression assays, which differ in terms of either or both the intervention which was carried out and the biological system upon which the intervention was carried out, correlations may be determined without it being necessary to determine the mechanism by which one or more interventions affect the expression profile of non-coding RNAs in one or more biological systems.

Thus, where a second intervention is found to have an effect on the expression profile of non-coding RNAs which is correlated with the effect of a first intervention which is of known therapeutic relevance, the second intervention can be treated as a candidate for the same or a similar therapeutic application. There is at least some possibility that the first and second interventions will have the same, a similar, or a related mechanism of action. This methodology is in direct contrast to known strategies for discovering therapeutic interventions, in which a specific target (such as a protein, nucleic acid or liquid molecule) is identified, and analysed, the biology of the target is studied in depth, and therapeutic interventions suitable to modulate one or more activities of the target are developed by rational and/or combinatorial methods.

One or more (and optionally all) said interventions may comprise the application of one or more test agent to a biological system, either simultaneously or sequentially. The one or more test agent may be a chemical entity, for example, a molecule having a molecular weight of less than 2,000 Daltons, less than 1,000 Daltons or less than 500 Daltons. The chemical entity may be non-polymeric. The one or more test entity may be a biological entity, for example, a biological macromolecule, such as a lipid, an oligonucleotide, or a protein (e.g. an enzyme, an antibody, or antibody fragment, humanized antibody or antibody fragment, phage or ribosome displayed protein fragment, or a prion). The biological entity may be a virus or bacteria. Thus, some or each of the expression assays may measure the effect of a test agent on the expression profile of non-coding RNAs in a biological system.

One or more said test agents may be a therapeutic agent. One or more said test agents may be a therapeutic agent having a known application to the treatment or prevention of a known condition. One or more said test agents may be a therapeutic agent which has been the subject of clinical trials (whether or not successfully) in relation to one or more indications. However, one or more (and optionally all) said interventions may comprise the application to a biological system of one or more of a group comprising: ionising radiation, continuously emitted or pulsed electromagnetic radiation (for example, visible light, ultra-violet light, infra-red light), acoustic energy (delivered through air or through a liquid medium), mechanical intervention (for example, the application of pressure), electricity, changes in temperature, changes in the osmolarity, tonicity or pH of a growth medium, magnetic fields, changes in fluid dynamics, and mechanochemical signal transduction. Thus, at least some interventions may be interventions which are known to be deleterious to the biological system. The expression profile resulting from such deleterious interventions may be useful to identify agents which reverse or prevent the deleterious effects.

One or more said biological systems may comprise cells, such as mammalian cells, for example, the cells of a human, a rabbit, or a rodent (for example a mouse or a rat), or cultured insect, amphibian or fish cell lines. One or more said biological systems may comprise a mixture of cell types. The intervention is typically carried out on cultured mammalian cells. The mammalian cells may be stem cells or progenitor cells. By stem cells we refer to cells which are capable of self-renewal and differentiation into at least one other specialised cell type. However, one or more said biological systems may be a whole organism, ex-vivo tissue, a synthetic system or transformed cells. The one or more said biological systems may be transgenic. Cultured cells may have synchronous or asynchronous cell cycles. One or more said interventions may be an intervention which changes the differentiation or de-differentiation state of a stem cell or progenitor cell, or which causes a stem cell or progenitor cell to specialise, or to replicate while maintaining the characteristics of a particular cell lineage or differentiation state.

The expression assays may be repeated and the expression data sets which are analysed may be compiled from some or all repeat experiments using equivalent interventions on equivalent biological systems.

Correlations are typically between the expression of a subset of the non-coding RNAs in connection with which expression data is stored in the expression data sets. Correlations between effects on the expression profile of non-coding RNAs are typically correlations, which may be positive or negative, in the change in the expression of one, or a small number of (e.g. two, three, five or fewer than five, or ten or fewer then ten) non-coding RNAs between two or more expression assays. A positive correlation may comprise an increase in the expression of one or more non-coding RNAs in each of two expression assays. A positive correlation may comprise a decrease in the expression of one or more non-coding RNAs in each of two expression assays. A negative correlation may comprise an increase in the expression of one or more non-coding RNAs in a first expression assay and a decrease in expression of the same one or more non-coding RNAs in a second expression assay.

In order to determine correlations between the effect on the expression profile of non-coding RNAs of a respective intervention, the method may further comprise measuring the expression profile of non-coding RNAs in a suitable control assay, for example a control assay in which the respective intervention is not carried out, or a control assay comprising measuring the expression profile of non-coding RNAs in a biological system prior to the respective intervention being carried out. Differences between the expression profile of non-coding RNAs in expression assays and corresponding control assays may be determined. The stored expression data set may be derived from a measured expression profile and an expression profile of a corresponding control assay. The step of analysing the resulting expression data may comprise taking into account expression profiles from control assays. However, in some applications it will not be necessary to carry out control assays. For example, if a plurality of interventions are carried out on equivalent biological systems it may be necessary only to analyse data sets derived solely from the expression profiles resulting from each expression assay to determine correlations between the effect on the expression profile of non-coding RNAs of the respective interventions.

It may be that at least some of the said correlations are positive correlations, for example, similarities between the effect on the expression of non-coding RNAs of the respective intervention in groups of two or more expression assays. The step of analysing the resulting expression data sets to determine correlations may include the step of categorising (for example, clustering or grouping) expression assays on the basis of similarities between the expression data sets resulting from expression assays. Advantageously, this may allow similarities in the mechanism by which two or more different interventions have an effect directly or indirectly on the expression profile of non-coding RNAs (typically on the same or equivalent biological systems) to be identified without a requirement for the nature of the shared mechanism to be understood.

Thus, the method may be a method of determining that two or more interventions have similar effects on the expression of one or more non-coding RNAs. A first intervention may be the application of a first therapeutic entity, having at least one known first therapeutic application, and the method may be a method of determining that there is a positive correlation between the effect on non-coding RNA expression of a second intervention, comprising the application of a second therapeutic entity. Accordingly, the method may be a method of determining a possible new therapeutic application (the first therapeutic application) for a known therapeutic entity (the second therapeutic entity). The method may further comprise the test of testing whether a second intervention is applicable to the treatment of a said known first therapeutic application.

The first intervention may be the application of an entity without a known first therapeutic application, but which is known to have pharmacological and toxicological profiles suitable for deployment as a therapy. Thus, the method may be a method of determining a possible new therapeutic application of a therapeutic entity which has passed toxicology trials but failed to be found to be efficacious, or more efficacious than a control therapeutic entity, in clinical trials.

It may be that at least some of the said correlations are negative correlations, for example, it may be determined that two or more interventions have opposite effects on the expression of one or more non-coding RNAs. Advantageously, a negative correlation between the effect on the expression profile of non-coding RNAs of a first intervention and a second intervention may indicate that the second intervention could possibly be useful to reverse one or more effects of the second intervention in therapy. Thus, the first intervention may be an intervention which is known to have a deleterious effect on the biological system, for example, the first intervention may be the application of a toxin. In this case, the method may comprise identifying the second intervention as a candidate for the treatment or prevention of a condition known to be caused by the first intervention.

Thus, a plurality of interventions may comprise the administration of a toxin or a treatment which is deleterious to the biological system. The method may therefore be part of a method of determining candidate interventions (e.g. candidate therapeutic entities) which may treat or prevent a condition known to be causable by one or more other interventions. The method may be a part of a method of determining candidates to treat or prevent side effects of known therapeutic interventions (e.g. the application of a therapeutic entity or a radiotherapy).

The method may be a method of predicting one or more aspects of the toxicity of a test agent, for example, by detecting that the expression profile of non-coding RNAs arising from a first intervention is positively correlated with the expression profile of an intervention which is known to have a deleterious effect on the biological system, or positively correlated with the expression profile of an intervention comprising the administration of an agent, one or more aspects of the toxicology of which are known.

The method maybe a method of determining that a first test agent is a candidate agonist or antagonist of a second test agent, or a specific target macromolecule, by determining a correlation respectively between the effect on the expression profile of non-coding RNA of the first test agent and the second test agent, or a test agent which is a known agonist or antagonist of the target molecule.

The method may comprise the step of grouping interventions which have similar effects on the expression of non-coding RNAs. The resulting expression profiles may be useful starting points for further research to identify further therapeutic entities. The method may be a method of determining changes in an expression profile of non-coding RNAs associated with a group of interventions, for example, a group of therapeutic entities. Thus, the method may be a method of determining that a chemical or biological entity has a mechanism of action on a biological system which is related to the mechanism of action of another chemical or biological entity on a biological system. Groups may be ordered in a hierarchy.

Where an intervention is the application of a second test agent to the biological system and the effect of the application of the second test agent on the non-coding RNA expression profile is found to be correlated (positively or negatively) to the effect of another first test agent on the biological system, which first test agent is known to be useful for the treatment or prevention of a first condition, the second test agent, or test agents obtained by modifying the second test agent, may be tested for efficacy in the treatment or prevention of the first condition, or a condition related to the first condition. Test agents which are found to be efficacious for the treatment or prevention of the first condition, or a condition related to the first condition, may be deployed from the treatment or prevention of the relevant condition.

In some embodiments, expression assays are carried out in which the same intervention, or group of interventions are carried out on a plurality of different biological systems. Thus, the method may enable the discovery of correlations between the effects of interventions which are present in only some of the plurality of different biological systems. In some embodiments, the plurality of different biological systems are stem cells in different states of differentiation or de-differentiation, for example, different stages of development. Thus, the method may enable the discovery of correlations between the effects of interventions on stem cells in specific states of differentiation or de-differentiation. This information is useful to investigate the mechanisms of development and stem cell or progenitor cell differentiation and de-differentiation. The plurality of different biological systems may comprise mammalian cells in different disease states. An intervention may be an intervention which causes stem cells or progenitor cells to differentiate or de-differentiate, or drive the attainment of a specific differentiation state or maintain the stability of stem cells or progenitor cells in a particular differentiation state.

The expression profile is related to the expression of at least one, and typically a plurality of non-coding RNAs, preferably at least 10, or more preferably at least 100 non-coding RNAs. The expression profile may be related to the expression of one or more transgenic non-coding RNAs functioning as markers. An expression profile may include quantitative or qualitative measurements of the level of expression of one or more non-coding RNAs. The level of expression of one or more said non-coding RNA may be determined indirectly via measurements of the amount or level of activation of a reporter construct, for example, a transgenic reporter construct incorporated into the genome of the biological system, or maintenance episomally, in a particular biological system. The expression profile is typically related to the amount of one or more non-coding RNAs which are expressed in at least some circumstances in the biological system, for example, the steady state or peak amount of the one or more non-coding RNAs. However, the expression profile may, for example, be related to the rate of change of expression of one or more non-coding RNAs. In some embodiments, the expression profiles are obtained using a microarray.

The non-coding RNAs typically include microRNAs (miRNAs) and may include either or both miRNA precursors and mature miRNAs. The non-coding RNAs may comprise one or more of small interfering RNAs (siRNA), piwi-interacting RNA (piRNA), small nuclear RNAs (snRNA), and short hairpin RNA (shRNA). The non-coding RNAs may be transgenic. Some or all of the RNAs may, for example, be transgenic RNAs which function as reporters of non-coding RNA expression. The non-coding RNAs may be episomal and the method may include the step of introducing episomal DNA into the biological system, for example by infection of a biological system with a virus, wherein the episomal DNA can be transcribed to produce non-coding RNA which constitute all or part of the profiled non-coding RNA.

Expression profiles may be measured for each non-coding RNA in a group of non-coding RNAs and the method may comprise identifying individual non-coding RNAs, or a subgroup of the group of non-coding RNAs, which have expression profiles on which a plurality of interventions have a correlated effect.

The plurality of interventions which have correlated effects may be identified by the method of the invention, thus enabling both interventions which have correlated effects on the expression profile of a group of non-coding RNAs and the individual non-coding RNAs or subgroup of non-coding RNAs within the group having expression levels which are affected by the plurality of interventions to be identified.

The plurality of interventions which have correlated effects may be interventions which are previously known to have a related mechanism of action, for example, the plurality of interventions may comprise the administration of agents known or believed to have the same or a similar mechanism of action, for example a class of drugs. Thus, the invention provides a method of identifying the individual non-coding RNAs or a subgroup of non-coding RNAs having expression levels affected by the plurality of interventions.

The resulting identified individual non-coding RNAs or identified sub-groups of non-coding RNAs may then be selected for use in further expression assays in which the expression profile of a reduced group of non-coding RNAs is measured, the reduced group of non-coding RNAs including only some of the group of non-coding RNAs, including, or optionally consisting of, at least the identified individual non-coding RNAs or identified sub-groups of non-coding RNAs. The effect of further interventions on the expression profile of the reduced group of non-coding RNAs and correlations between the effect of further interventions on the expression profile of the reduced group of non-coding RNAs and the effect of the said plurality of interventions on the expression profile of the reduced group of non-coding RNAs can be thereby determined. Thus, subsequent assays and tests may employ fewer non-coding RNAs, reducing costs and increasing throughput. For example, a reduced group of non-coding RNAs having expression levels upon which a class of therapeutic agents have a correlated effect may be used to screen candidate agents, either to find novel therapeutically useful agents or to identify new indications for known therapeutic agents.

The relevance of the expression level of a group or subgroup of non-coding RNAs to discrimination between the effect of biological interventions may be determined. The method may comprise the step of ranking non-coding RNAs within the group or sub-group depending on their relevance to discrimination between the effects of biological interventions. The method may comprise the step of ranking the effect on the expression of non-coding RNAs in a group or sub-group of non-coding RNAs of a biological intervention, or a group of biological interventions having a correlated effect on the expression of non-coding RNAs. The resulting rankings may be used to identify correlations between the effects of biological interventions.

Correlations may be identified by statistical mathematical methods, for example, principle component analysis. The effect of a biological intervention on the expression of each of a plurality of specific non-coding RNAs may be allocated one of a group of codes indicative of properties of the effect of the biological intervention on the expression of the respective non-coding RNA. The resulting codes may be analysed to identify correlations.

The invention also extends to assay apparatus (for example a test kit or a solid phase support having non-coding RNAs immobilised thereto) having non-coding RNAs consisting of a said reduced group of non-coding RNAs, obtained by the method of the invention.

DESCRIPTION OF THE DRAWINGS

An example embodiment of the present invention will now be illustrated with reference to the following Figure in which:

FIG. 2 is a plot of the results from principal component analysis for one biological intervention (a) and for one variable (b);

FIG. 4 is a plot of data from principal component analysis showing (a) a labelled sub-group of discriminatory miRNAs, and (b) data from four intervention types showing how the expression data from different intervention types cluster.

DETAILED DESCRIPTION OF AN EXAMPLE EMBODIMENT

Figure 1:
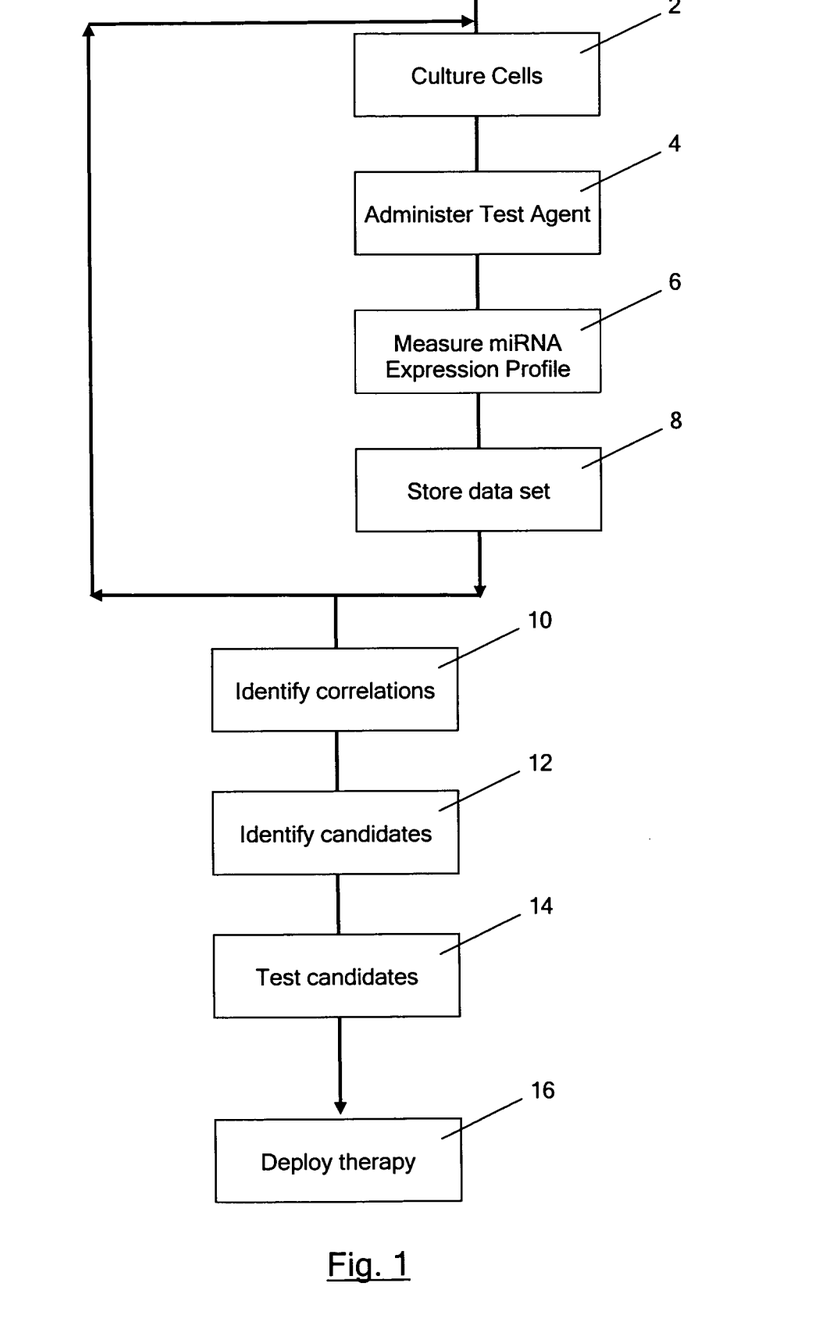
FIG. 1 is a flow diagram of a method according to the invention.

In an example application of the invention, a database of miRNA expression data sets (being an example of an expression data set derived from a measured non-coding RNA expression profile) is prepared. With reference to FIG. 1, suitable human cells are cultured 2 by known methods and a test agent is administered 4 to the cultured cells. A miRNA expression profile is then measured 6 using a sample of the treated cells, at one or more periods of time after the intervention is made, to determine the expression level of each of a number of miRNAs in the treated cells.

Two alternative methods for measuring the miRNA expression profiles, microarray analysis and qualitative real-time PCR analysis, are set out below.

(1) miRNA Microarray and Data Analysis

Total RNA from drug-treated (n=3) and control treated cells (n=3) are isolated using a column-based kit from Exiqon A/S of Vedbaek, Denmark. Two µg of total RNA from each sample is analysed by miRNA microarray. miRNA microarray analysis including labelling, hybridization, scanning, normalization and data analysis is commercially available from a number of sources, for example, from Exiqon A/S. Briefly, RNA Quality Control is performed using Bioanalyser 2100 microfluidics platform (Bioanalyser is a trade mark of Agilent Technologies). Samples are labelled using the Complete Labelling Hyb Kit from Agilent, following the provided instructions.

(2) Quantitative Real-Time PCR

As with option (1) above, all cellular RNA is extracted using a column-based kit from Exiqon and following the manufacturer's instructions. Quantification of miRNAs by TaqMan Real-Time PCR is carried out as described by the manufacturer (Applied Biosystems of Foster City, Calif., USA). (TaqMan is a trade mark of Roche Molecular Systems, Inc.). Briefly, 10 ng of RNA is used as a template for reverse transcription (RT) using the TaqMan MicroRNA Reverse Transcription Kit and miRNA-specific stem-loop primers (Applied Biosystems). An aliquot (1.5 µl) of the RT product is introduced into 20 µl PCR reactions which are incubated in 96-well plates on the ABI 7900HT thermocycler (Applied Biosystems) at 95° C. for 10 min, followed by 40 cycles of 95° C. for 15 s and 60° C. for 1 min. Target gene expression is normalized between different samples based on the values of U48 RNA (a small, non-coding RNA) expression (or GAPDH, if U48 is found to vary with drug treatment).

In each case, the resulting miRNA expression levels are stored as 8 expression data sets. A large number of expression assays are preferably carried out. Typically, many (e.g. hundreds or thousands) of test agents are introduced to cell cultures and analysed in this way to create a database of miRNA expression data.

Once a suitably large database of miRNA expression data sets are available, the expression data sets are analysed 10 to determine correlations between the effects of each test agent on miRNA expression and to create hierarchical clusters of test agents which have similar effects on the miRNA expression profiles.

Methods for determining correlations between nucleic acid expression data sets are well known to those skilled in the art. For example, one method is to import microarray data obtained from Exiqon A/S in the GPR format into a spreadsheet. (GPR is the data format used by Genepix6 software, available from Molecular Devices of Union City, Calif., USA. Genepix is a trade mark of Molecular Devices). Spot intensities for each miRNA are analysed against quality control and calibration spots provided on the miRNA array (indicated by Genepix6 software as a negative flag). Values with signal intensities below 50 are brought up to 0. For each of the four replicate spots for each miRNA capture probe species, the median value of the background corrected spot intensity is calculated and imported into TMeV microarray analysis software which performs hierarchical clustering and/or other statistical analyses familiar to one skilled in the art. (TMeV is provided by the Dana-Farber Cancer Institute, at the URL www.tm4.org).

Alternatively, GRP format expression data may be imported into Genespring GX software, available from Agilent Technologies. (Genespring GX is a trade mark of Agilent Technologies), normalised to the $75^{th}$ percentile and then processed using hierarchial clustering and other statistical tools built into Genespring GX.

Where positive correlations are found between the effects of two or more test agents on the expression of one or more miRNAs, this may be indicative that the test agents share the same, or a related, mechanism of action. Thus, test agents which are found to have similar effect on miRNA expression profile as an agent which is known as a treatment for a condition can be identified 12 as candidates for treatment of the same, or a related condition. This may be useful to facilitate the repositioning of drugs which have already been identified as potentially useful for one therapeutic application. Candidate test agents can be tested to determine whether they may be useful for treatment of the same, or a related condition, or used as the starting point for further research. For example, they might be modified using rational or combinatorial design methodologies, a mimetic compound might be prepared and tested and so forth. Candidate test agents can be tested 14 to determine whether they are suitable for use as therapeutic entities and, if, they are, deployed 16 as therapeutic entities.

It is especially useful to group test agents which have similar effects on the expression of one or more miRNAs as this classification by effect on miRNA expression may be reflected in a similar or related mechanism of action, whether direct or indirect, on miRNA expression levels.

Where negative correlations are identified, one test agent might be identified as a candidate to prevent, mitigate or obviate one or more undesirable affects of a further test agent or other intervention. Thus, a test agent which is known to have an opposite effect on the expression of one or more miRNAs to another test agent which has an undesirable effect could be considered as a candidate entity for the treatment or prevention of that undesirable effect.

Advantageously, miRNA expression assays are carried out to assess the effect of a range of interventions, including interventions other than the administration of a chemical or biological entity. For example, cells may be treated with ultraviolet light, ionising radiation, acoustic waves and other interventions which are deleterious to the cells. Where a test agent can be identified which has an effect on the expression of one or more miRNAs which is negatively correlated to the effect of such interventions, the test agent may be a candidate for the treatment or prevention of undesirable effects resulting from a corresponding intervention in vivo. This may be useful to identify agents for the prevention of damage caused by ultraviolet light or as side effects from radiotherapies.

The method can be applied to the high-throughput screening of large numbers of test agents (e.g. combinatorial libraries of small chemical entities, peptides, peptidomimetics or polynucleic acids). As new expression assays are carried out the resulting expression data sets can be compared against previously stored expression data sets to look for correlations between the effects of screened test agents and agents which have been previously assayed.

The method is typically best employed using a large database of miRNA expression data sets. However, for some specific applications it may only be necessary to have a small number of miRNA expression data sets, or even one miRNA expression data set, available for comparison with the miRNA expression data set resulting from a new assay. This may be relevant in high-throughput screens to find agents which have an effect on miRNA expression which correlates positively or negatively with a particular identified effect, for example, the effect of an agent which is known or suspected as having a significant effect on miRNA expression.

Thus, the invention is based on a principle that similarities in mechanism of action, and therefore practical applications, of test agents (such as chemical entities and biologics) may be found through the comparative analysis of their effects on the expression of miRNAs (and potentially other non-coding RNAs) without it being essential to understand the mechanism through which the test agents affect miRNA expression profiles. This is in direct contrast to conventional drug discovery and drug repositioning strategies in which a mechanism of action is researched in depth to identify a drug target for use in screening assays to discover agents which have a desired interaction with the drug target.

Experimental Findings and their Implications

Using the methods described we have determined that it is possible to determine potential modes of therapeutic application of interventions based on the grouping of miRNA expression data. Furthermore, the method can be employed to identify certain miRNAs, having expression levels which are indicative of certain therapeutic applications for interventions being screened. Such indicative miRNAs will enable future intervention screening to analyse a relatively small group of miRNA expression levels to identify potential therapeutic applications of the interventions being screened, and not the entire miRNA library.

An example of using a select small group of miRNAs to determine potential therapeutic uses for an intervention is given below.

During experiments described here, by way of a control, a group of cells were treated with a drug solvent mix comprising dimethyl sulphoxide, or DMSO, and phosphate buffered saline. It was assumed that the drug solvent mix would not have an effect on miRNA expression, and if it did, it would not be consistent with any of the patterns associated with the drugs being tested. However, the drug solvent mix was found to have a miRNA expression pattern consistent with an HDAC inhibitor. Subsequently, it was found from a literature review that DMSO had been shown to be an HDAC inhibitor, confirming that unknown potential therapeutic properties of drugs can be determined using the methods of the invention.
Materials and Methods HeLa cells were cultured using standard methods. The cells were split into DMEM medium.

The media was aspirated and the cell monolayer was washed with an appropriate amount of Phosphate Buffered Saline (PBS, 8 g NaCl, 0.2 g KCl, 1.44 g $Na_2HPO_4$ and 0.24 g $KH_2PO_4$ dissolved in 800 ml of distilled $H_2O$). The PBS was aspirated.

The test agent in question was administered to the cells and incubated for 48 hours.

RNA Extraction

RNA was isolated and purified from these cells using a column-based kit from Exiqon the following procedure.

The medium the cells were grown on was aspirated and the cell monolayer was washed with an appropriate amount of PBS. The PBS was further aspirated.

350 μL of the lysis solution was added directly to a culture plate. The cells were lysed by gently tapping the culture dish and swirling buffer around the plate surface for five minutes. The lysate was then transferred to a micro-centrifuge tube.

200 μL of 95-100% ethanol was added to the lysate and mixed by vortexing for 10 seconds.

A column was assembled using one of the tubes provided in the kit. 600 μL of the lysate/ethanol was applied onto the column and centrifuged for 1 minute at 14,000×g. The flow-through was discarded and the spin column was reassembled with its collection tube.

400 μL of the supplied wash solution was applied to the column and centrifuged for 1 minute at 14,000×g. The flow-through was discarded and the spin column was reassembled with its collection tube.

The column was washed twice more by adding another 400 μL of wash solution and centrifuging for 1 minute at 14,000× g. The flow-through was discarded and the spin column was reassembled with its collection tube.

The column was spun for two minutes at 14,000×g to thoroughly dry the resin and the collection tube was discarded.

The column was assembled into a 1.7 mL elution tube provided with kit. 50 μL of elution buffer was added to the column and centrifuged for two minutes at 200×g followed by one minute at 14,000×g.

The resulting purified RNA sample could be stored at −20° C. for a few days. For long-term storage of samples were stored at −70° C.

(1) miRNA Microarray and Data Analysis
Labelling

Purified RNA samples were labelled using a labelling kit from Agilent.

The total RNA sample was diluted to 50 ng/μL in 1×TE pH 7.5. 2 μL of the diluted total RNA was added to a 1.5 mL micro-centrifuge tube and put on ice. Immediately prior to use, 0.4 μL 10×calf intestinal phosphatase buffer, 1.1 μL nuclease free water and 0.5 μL calf intestinal phosphatase were gently mixed to prepare a calf intestinal alkaline phosphatase master mix.

2 μL of the calf intestinal alkaline phosphatase master mix was added to each sample tube for a total reaction volume 4 μL, and was gently mixed by pipetting. The reaction volume was incubated at 37° C. in a circulating water bath for 30 minutes.

2.8 μL of 100% DMSO was added to each sample. Samples were incubated at 100° C. in a circulating water bath for 5-10 minutes and then immediately transferred to an ice bath.

10×T4 RNA ligase buffer was warmed to 37° C. and spun until all precipitate had dissolved. Immediately prior to use, 1 μL of 10×T4 RNA ligase buffer, 3 μL cyanine3-pCp and 0.5 μL T4 RNA ligase were gently mixed to make a ligation master mix and put on ice.

4.5 μL of the ligation master mix was added to each sample tube for a total reaction volume of 11.3 μL. Samples were gently mixed by pipetting and spun down. The samples were then incubated at 16° C. in a circulating waterbath for two hours. The samples were then dried using a vacuum concentrator at 45-55° C. and the samples were determined to be dry if, when the tube was flicked the pellets did not move or spread.

Hybridization

125 μL of nuclease free water was added to the vial containing lyophilised 10×GE blocking agent supplied with the Agilent Kit and mixed.

The dried sample was resuspended in 18 μL of nuclease free water. 4.5 μL of the 10×GE blocking agent was added to each sample. 22.5 μL of 2×Hi-RPM Hybridization buffer was added to each sample and mixed well. The resulting samples were incubated at 100° C. for 5 minutes, and then immediately transferred to an ice waterbath for a further 5 minutes.

A clean gasket slide was loaded into the Agilent SureHyb chamber base ensuring the gasket slide was flush with the chamber base. The hybridization sample was dispensed onto the gasket well ensuring no bubbles were present.

An array was placed active side down onto the SureHyb gasket slide and assembled with the SureHyb chamber cover to form an assembled chamber. The assembled chamber was placed into a hybridization oven set at 55° C. and rotated at 20 rpm for 20 hours at that temperature.

The arrays were subsequently washed using the supplied GE wash buffers before being scanned.

(2) Quantitative Real-Time PCR
Preparing the RT Reaction Master Mix

The components were thawed from frozen on ice. The RT reaction master mix was prepared by mixing 0.15 μL dNTPs (100 mM), 1 μL MultiScribe Reverse Transcriptase (MultiScribe is a trade mark of Applera Corporation) (50 U/μL), 1.5 μL 10× Reverse Transcription Buffer, 0.19 μL RNase Inhibitor (20 U/μL), 4.16 μL nuclease-free water, and then stored on ice. Note that the volumes quoted above are per 15 μL RT reaction and were scaled up for the number of RT reactions to be carried out.

Preparing the RT Reaction

For each 15 μL RT reaction, 7 μL RT master mix was combined with 5 μL total RNA. The RT Primers were thawed on ice and 3 μL of RT primer was added to the 12 μL of the RT master mix/total RNA in a 96-well plate well. The plate was kept on ice until filled and then put into the thermal cycler.

Thermal Cycler steps:
  16° C. for 30 minutes
  42° C. for 30 minutes
  85° C. for 5 minutes
  4° C. for as long as convenient PCR Amplification For each well, 10 μL Taqman 2× Universal PCR Master Mix was mixed with 7.67 μL nuclease-free water, 1 μL of 20× Taqman MicroRNA Assay mix and 1.33 μL of the RT product from the previous step. When all the wells were filled the plate was sealed with an optical adhesive cover and centrifuged to remove any air bubbles.

The plate was then loaded into a real-time capable thermal cycler/PCR machine and the following program followed:
  95° C. for 10 minutes (Activation of the AmpliTaq Gold Enzyme)
  40×(95° C. for 15 seconds, 60° C. for 60 seconds).

Data Analysis

Data from both of these techniques was normalised against the spike-in miRNA spots for each plate, allowing data from separate arrays to be compared.

Normalised data was analysed using Principal Component Analysis, a standard technique well understood by those skilled in the art to identify correlations between miRNA expression profiles, and any grouping of data observed determined to be a consequence of the action of the particular test agent applied to the original cells on the expression of the individual miRNA.

FIG. 1 is a flow diagram of a method for obtaining an expression profile for micro RNA.

Figure 2A:
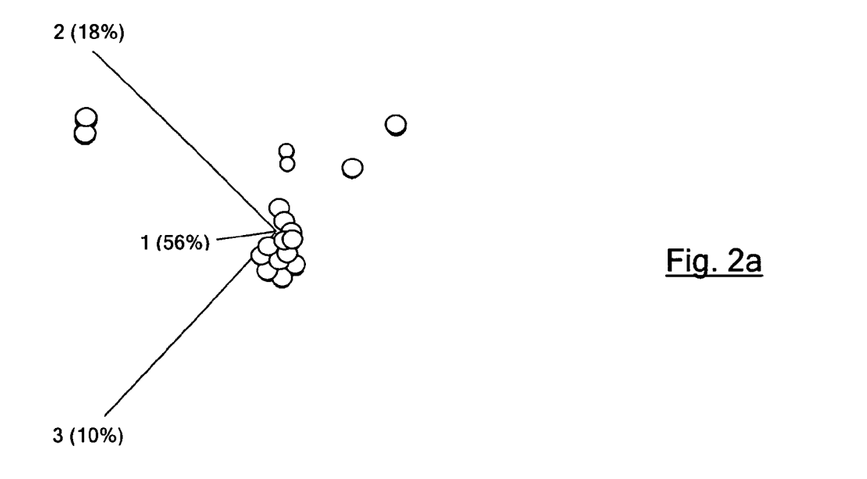
Figure 2B:
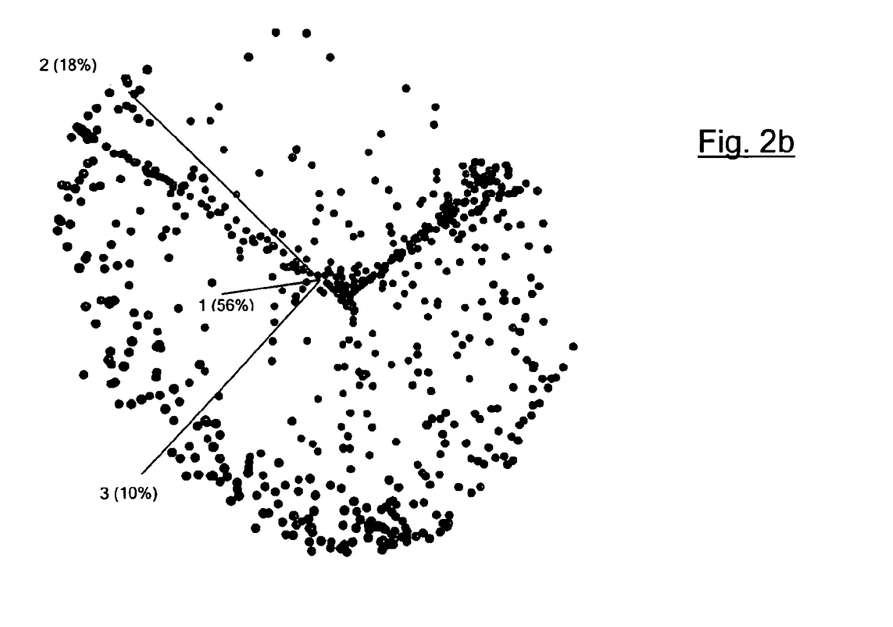
Figure 3:
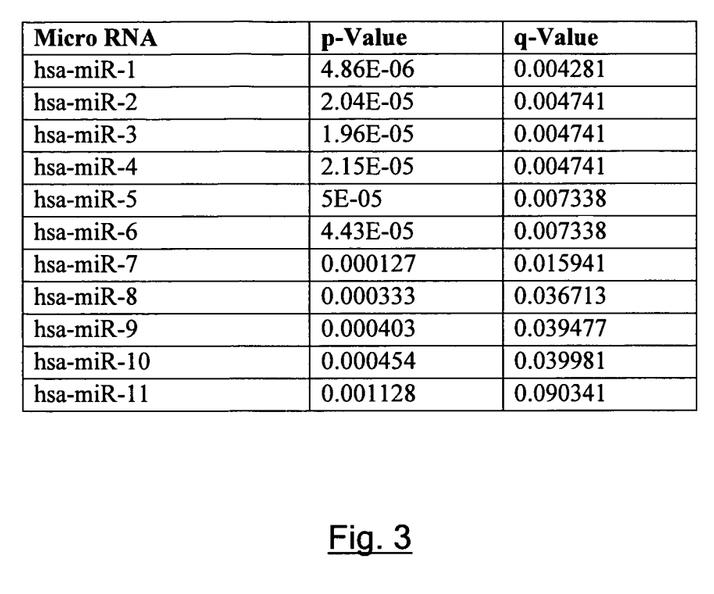
FIG. 3 is a table giving statistical rankings of 11 miRNAs by their p-value and q-value.

FIG. 2 shows an example of an expression profile after principal component analysis. Part (a) shows a three dimensional projection of three principal components of the total multidimensional expression data set of miRNA expression and illustrates clustering of miRNA expression data for one treatment type. Part (b) shows the data spread for the expression of single miRNA exp FIG. 3 shows a statistical ranking of 11 discriminatory miRNAs labelled has-miR-1 through has-miR-11. The p-value is the standard statistical test value of whether a result is statistically significant or the result of chance (generally given to be a p-value of ≤0.05) and the q-value being the p-value corrected for multiple testing and provides a measure of the false discovery rate. All p-values shown are much less than 0.05.

Figure 4A:
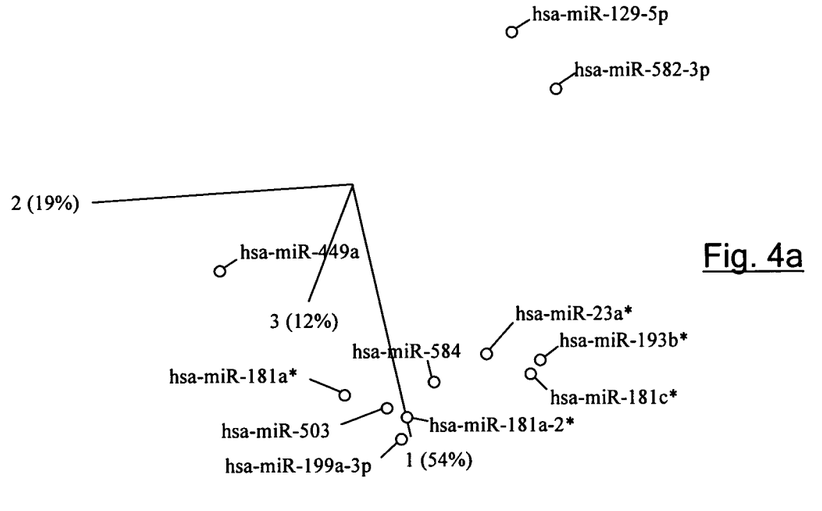
Figure 4B:
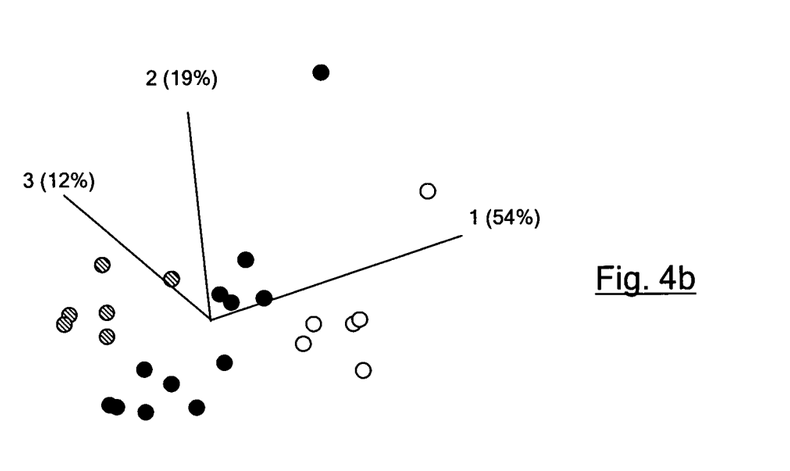

FIG. 4 (*a*) shows a projection of three principal components of the multidimensional data set for miRNA expression for multiple miRNAs and the clustering of miRNAs indicative of a potential therapeutic applications. (*b*) shows a projection of three principal components of the multidimensional data set for miRNA expression for multiple miRNAs wherein the individual miRNAs are shaded to indicate the therapeutic application for which the biological intervention applied in their expression is used.

As can be seen, the results are clearly grouped and that this grouping is according to the therapeutic use of the biological intervention applied to the cells in which the miRNAs were expressed. In other words, it is possible to determine that the grouped biological interventions may have a similar mechanism of action upon the cells to which they were applied, and the shared mechanism resulted in similar effects on miRNAs expression levels.

Biological interventions with similar mechanisms of action may also have similar therapeutic properties and therefore they may have similar therapeutic applications. Data presented in FIGS. 3 and 4 demonstrates that for the biological interventions tested, the projection of three principal components of the multidimensional data set for miRNA expression for biological interventions of similar therapeutic application (for example, anti-metabolites) did indeed group together, and that the groupings of biological interventions with a different therapeutic use (for example epigenetic modifiers) were grouped separately.

A database of miRNA expression patterns can be built up by carrying out many biological interventions and analysing the resulting changes in miRNA expression profile. Such a database would enable identification of the therapeutic use, or potential future therapeutic use, of an untested biological intervention by comparing a miRNA expression profile of said untested biological intervention with that in the database and determining whether the said expression profile falls within one of the therapeutic application groupings. If such a correlation occurs, the untested biological intervention may be considered for that specific therapeutic application.

Furthermore, building up a database of miRNA expression data may reveal a subset of certain miRNAs that are indicative of a certain therapeutic application. Once said subset of indicative miRNAs are identified, future testing of new biological interventions to find potential therapeutic applications, or testing known biological interventions for new therapeutic applications, can be carried out by looking at the expression profiles of the subset of indicative miRNA expression profiles and not the entire range of miRNAs produced by the cells.

The database of miRNA expression data may also be employed to determine a subset of certain miRNAs, the expression levels of which are most useful for discriminating between biological interventions, or between groups of biological interventions known or hypothesized to have similar modes of action. miRNAs may be ranked in order of the relevance of their expression levels for discriminating between biological interventions, or between groups of biological interventions known or hypothesized to have similar modes of action. miRNAs may be allocated a numerical value indicative of the relevance of their expression levels for discriminating between biological interventions, or between groups of biological interventions known or hypothesized to have similar modes of action. For example, the numerical value may be related to the contribution of the expression level of an miRNA to the variance of principle components.

As an alternative to, or in addition to, the comparison of miRNA expression profiles using statistical methods such as principal component analysis, the effect of a biological intervention on the expression of each of a limited group of miRNAs (for example, 10-50) may be identified and used to assign a code, selected from a group of codes, to the effect of the biological intervention on the expression of each respective miRNA. The resulting codes may be compared to identify similarities in effect.

For example, for each biological intervention (e.g. for each screened compound) a 3-digit binary number may be allocated as a code to each ranked miRNA based on:

1. If expression of the miRNA is unchanged (within normal limits of experimental variability) in response to the biological intervention, the first bit is set to 0. If expression has changed significantly, the first bit is set to 1.

2. If a change in expression level was identified and the change was an increase, the second bit is set to 1. If the change resulting from the biological intervention was a decrease, the second bit is set to 0.

3. If the change in expression level was more than 4-fold, the third bit is set to 1, otherwise it is set to 0.

Thus, the effect of a biological intervention level on the expression of an miRNA is allocated a code having one of five possible values:

1. No change in expression—000
2. Large increase in expression—111
3. Small increase in expression—110
4. Large decrease in expression—101
5. Small decrease in expression—100

The effect of a biological intervention (for example, the administration of a particular compound) on the expression level of a group of miRNAs may be characterised by the associated code, permitting identification of changes in expression level not immediately apparent from principal component analysis, permitting alternative methods of scoring the similarity of biological interventions and rendering the resulting expression data comprehensible by visual inspection.

Another way to characterise the effect of a biological intervention and to determine correlations between the effects on miRNA expression of different biological interventions is to carry out an expression assay to determine the effects of a biological intervention on the expression of each of a group (of typically 10 to 50) miRNAs and to rank the miRNAs in that group in order of the effect, for example, in order from the miRNA in the group which has the largest increase in expression to the miRNA in the group which has the largest decrease in expression, or vice versa. The resulting rankings are indicative of the effects of particular biological interventions. Thus, the effect of other biological interventions on the group of miRNAs may be measured and the miRNAs in the group ranked in order of the effect. The resulting rankings may be compared to enable correlations between the effect of biological interventions to be identified.

A kit comprising plates operable to test the subset of indicative miRNAs may be provided to significantly increase the efficiency and speed with which biological interventions can be screened for potential novel therapeutic applications.

Further variations and modifications may be made within the scope of the invention herein disclosed.

REFERENCES

1. Xie, X., et al., Systematic discovery of regulatory motifs in human promoters and 3'-UTRs by comparison of several mammals. Nature, 2005. 434(7031): p. 338-45
2. Lim, L. P., et al., Microarray analysis shows that some microRNAs downregulate large numbers of target mRNAs. Nature, 2005. 433(7072): p. 769-73
3. Calin, G. A., et al., MicroRNA profiling reveals distinct signatures in B cell chronic lymphocytic leukemias. Proc Natl Acad Aci USA, 2004. 101 (32): p. 11755-60

The invention claimed is:

1. A method for identifying a group of miRNAs for use in expression assays, the method comprising the steps of:
   (1) carrying out a plurality of expression assays, each expression assay comprising the steps of: carrying out at least one intervention on a biological system comprising cultured cells or ex vivo tissue, measuring an expression profile of a group of miRNAs in the biological system resulting from the at least one intervention, and storing an expression data set derived from the measured expression profile, the said expression assays concerning a plurality of different interventions;
   (2) analysing the resulting expression data sets to determine correlations between the effect on the expression profile of miRNAs of the at least one intervention in groups of two or more expression assays concerning the plurality of different interventions;
   (3) identifying a sub-group of the group of miRNAs having expression profiles on which the plurality of different interventions have a correlated effect; and
   (4) selecting the sub-group of miRNAs for use in further expression assays in which the expression profile of a reduced group of miRNAs is measured, the reduced group including only some of the group of miRNAs including at least the identified sub-group of miRNAs,
   wherein the at least one intervention comprises the application to the biological system of at least one of a group comprising: ionizing radiation; continuously emitted or pulsed electromagnetic radiation; acoustic energy; mechanical intervention; the application of pressure, magnetic fields, or electricity; changes in temperature; changes in osmolarity, tonicity or pH of a growth medium; changes in fluid dynamics; and mechanochemical signal transduction.

2. The method according to claim 1, wherein the group of miRNAs comprises at least 100 miRNAs and wherein the sub-group of miRNAs consists of ten or fewer than ten miRNAs.

3. The method according to claim 1, wherein the biological system comprises cultured mammalian cells.

4. The method according to claim 3, wherein the cultured mammalian cells are stem cells or progenitor cells.

5. A method for identifying a group of miRNAs for use in expression assays, the method comprising the steps of:
   (1) carrying out a plurality of expression assays, each expression assay comprising the steps of: carrying out at least one intervention on a biological system comprising cultured cells or ex vivo tissue, measuring an expression profile of a group of miRNAs in the biological system resulting from the at least one intervention, and storing an expression data set derived from the measured expression profile, the said expression assays concerning a plurality of different interventions;
   (2) analysing the resulting expression data sets to determine correlations between the effect on the expression profile of miRNAs of the-at least one intervention in groups of two or more expression assays concerning the plurality of different interventions;
   (3) identifying a sub-group of the group of miRNAs having expression profiles on which the plurality of different interventions have a correlated effect; and
   (4) selecting the sub-group of miRNAs for use in further expression assays in which the expression profile of a reduced group of miRNAs is measured, the reduced group including only some of the group of miRNAs including at least the identified sub-group of miRNAs,
   wherein the at least one intervention comprises an intervention other than the administration of a chemical or biological entity.

* * * * *